United States Patent [19]
Munger, Jr. et al.

[11] Patent Number: 5,935,946
[45] Date of Patent: Aug. 10, 1999

[54] NUCLEOTIDE ANALOG COMPOSITION AND SYNTHESIS METHOD

[75] Inventors: John D. Munger, Jr., Alviso; John C. Rohloff, Mountain View; Lisa M. Schultze, San Carlos, all of Calif.

[73] Assignee: Gilead Sciences, Inc., Foster City, Calif.

[21] Appl. No.: 08/900,752

[22] Filed: Jul. 25, 1997

[51] Int. Cl.$^6$ .................................................. A61K 31/675
[52] U.S. Cl. ............................................ 514/81; 544/244
[58] Field of Search ................................ 514/81; 544/244

[56] References Cited

U.S. PATENT DOCUMENTS

| | | |
|---|---|---|
| 4,476,248 | 10/1984 | Gordon et al. . |
| 5,618,964 | 4/1997 | Cheng et al. . |
| 5,663,159 | 9/1997 | Starrett, Jr. et al. ................... 514/181 |

FOREIGN PATENT DOCUMENTS

| | | |
|---|---|---|
| 0 481 214 A1 | 4/1992 | European Pat. Off. . |
| 0 647 649 A1 | 4/1995 | European Pat. Off. . |
| WO 92/09611 | 6/1992 | WIPO . |
| WO 95/07920 | 3/1995 | WIPO . |
| WO 96/18605 | 6/1996 | WIPO . |

OTHER PUBLICATIONS

Ikeda et al., "Studies on Prodrugs. III. A Convenient and Practical Preparation of Ampicillin Prodrugs", 32:4316–4322, Chem Pharm Bull, 1984.
Jones et al., "Minireview: nucleotide prodrugs", 27:1–17, Antiviral Res, 1995.
Krise et al, "Prodrugs of phosphates, phosphonates, and phosphinates", 19:287–310, Advanced Drug Delivery Reviews, May 22, 1996.
Alexander et al., "Investigation of (Oxodioxolenyl)methyl Carbamates as Nonchiral Bioreversible Prodrug Moieties for Chiral Amines," J Med Chem 39:480–486 (1996).
Berge et al., "Pharmaceutical Salts," J Pharm Sci 66(1):1–19 (Jan. 1977).
Flaherty et al., "Synthesis and Selective Monoamine Oxidase B–Inhibiting Properties of 1–Methyl–1,2,3, 6–tetrahydropryrid–4–yl Carbamate Derivatives: Potential Prodrugs of (R)– and (S)–Nordeprenyl," J Med Chem 39:4759–4761 (1996).
Hammer et al., "Ether, Carbonate and Urethane Deoxynucleoside Derivatives as Prodrugs," Acta Chemica Scandinavia 50:609–622 (1996).
Iyer et al., "Synthesis of Acyloxyalkyl Acylphosphonates as Potential Prodrugs of the Antiviral, Trisodium Phosphonoformate (Foscarnet Sodium)," Tet Lett 30(51):7141:7144 (1989).
Landgrebe, John A., "Crystallization and Filtration," Theory and Practice in the Organic Laboratory 3rd edition, pp. 65–77 (1982).
Maillard et al., "Adenosine Receptor Prodrugs: Synthesis and Biological Activity of Derivatives of Potent, A1–Selective Agonists," J Pharm Sci 83(1):46–53 (Jan. 1994).
Myerson, Allan S. (editor), "Solutions and Solution Properties," Handbook of Industrial Crystallization pp. 1–165 (1993).
Starrett et al, "Synthesis and in vitro evaluation of a phosphonate prodrug: bis(pivaloyloxymethyl) 9–(2–phosphonylmethoxyethyl)adenine," Antiviral Res 19:267–273 (1992).
Starrett et al., "Synthesis, Oral Bioavailability Determination, and in Vitro Evaluation of Prodrugs of the Antiviral Agent 9–[2–(Phosphonomethoxy)eth]adenine (PMEA)," J Med Chem 37:1857–1864 (1994).
Tsai et al., "Effects of (R)–9–(2–Phosphonylmethoxypropyl)adenine Monotherapy on Chronic SIV Infection in Macaques," Aids Res & Hum Retro 13(8):707–712 (1997).
Benzaria et al., "New Prodrugs of 9–(2–Phosphonomethoxyethyl) Adenine [PMEA]: Synthesis and Stability Studies," Nucls & Nuclt 14(3–5):563–565 (1995).
Raic et al., "The Novel 6–(N–Pyrrolyl)Purine Acyclic Nucleosides: 1H and 13C NMR and X–Ray Structural Study," Nucls & Nuclt 15(4):937–960 (1996).
Sueoka et al., "Pharmacokinetics of Alkoxycarbonyloxy Ester Prodrugs of PMPA in Dogs," American Association of Pharmaceutical Science, Western Regional Meeting, Apr. 24–25, 1997 Abstract ( ).
Sueoka et al., "Pharmacokinetics of Alkoxycarbonyloxy Ester Prodrugs of PMPA in Dogs," American Association of Pharmaceutical Science, Western Regional Meeting, Apr. 24–25, 1997 Poster ( ).

(List continued on next page.)

*Primary Examiner*—James H. Reamer
*Attorney, Agent, or Firm*—Max D. Hensley

[57] ABSTRACT

The invention provides a composition comprising bis(POC) PMPA and fumaric acid (1:1). The composition is useful as an intermediate for the preparation of antiviral compounds, or is useful for administration to patients for antiviral therapy or prophylaxis. The composition is particularly useful when administered orally. The invention also provides methods to make PMPA and intermediates in PMPA synthesis. Embodiments include lithium t-butoxide, 9-(2-hydroxypropyl) adenine and diethyl p-toluenesulfonylmethoxyphosphonate in an organic solvent such as DMF. The reaction results in diethyl PMPA preparations containing an improved by-product profile compared to diethyl PMPA made by prior methods.

20 Claims, 7 Drawing Sheets

OTHER PUBLICATIONS

Tsai et al., "Prevention of SIV Infection in Macaques by (R)-9-(2-Phosphonylmethoxypropyl)adenine," Science 270:1197–1199 (Nov. 17, 1995).

Ueda, N. et al., "Vinyl Compounds of Nucleic Acid Bases. I. Synthesis of N-Vinyluracil, N-Vinylthymine, and N-Vinyladenine," Die Makromolekulare Chemie 120:13–20 (1968).

Arimilli et al., "Synthesis, in vitro biological evaluation and oral bioavailability of 9-[2-(phosphonomethoxy)propyl]adenine (PMPA) prodrugs", 8(6):557–567, Antiviral Chem & Chemo, 1997.

Arimilli et al., "Orally Bioavailable Acyclic Nucleoside Phosphonate Prodrugs: Adefovir Dipivoxil and Bis(POC)PMPA", vol. 3 (accepted for publication), ADV Antiviral Drug Design, 1998.

Robinson et al, "Discovery of the Hemifumarate and (alpha-L-Alanyloxy)methyl Ether as Prodrugs of an Antirheumatic Oxindole: Prodrugs for the Enolic OH Group", 39:10–18, J Med Chem, 1996.

Safadi et al, "Phosphoryloxymethyl Carbamates and Carbonates—Novel Water-Soluble Prodrugs for Amines and Hindered Alcohols", 10(9):1350–1355, Pharm Res, 1993.

Sakamoto et al, "Studies on Prodrugs. II. Preparation and Characterization of (5-Substituted 2-Oxo-1,3-dioxolen-4-yl)methyl Esters of Ampicillin", 32(6):2241–2248, Chem Pharm Bull, Aug. 19, 1983.

Shaw et al., "Metabolism and Pharmacokinetics of Novel Oral Prodrugs of 9-[(R)-2-(phosphonomethoxy)propyl]adenine (PMPA) in Dogs", 14(12):1824–1829, Pharm Res, 1997.

Srivastva et al, "Bioreversible Phosphate Protective Groups: Synthesis and Stability of Model Acyloxymethyl Phosphates", 12:118–129, Bioorg Chem, 1984.

De Clercq et al., "(S)-9-(2,3-dihydroxypropyl)adenine: An Aliphatic Nucleoside Analog with Broad-Spectrum Antiviral Activity", 200:563–565, Science, 1978.

Lindahl et al., "Synthesis of an Acyloxymethyl Prodrug of the Inositol Phosphate Alpha-Trinositol", 15(5):549–554, J Carbohydrate Chemistry, 1996.

Samara et al., "Pharmacokinetic Analysis of Diethylcarbonate Prodrugs of Ibuprofen and Naproxen", 16:201–210, Biopharmaceutics & Drug Disposition, 1995.

NUCLEOTIDE ANALOG COMPOSITION AND SYNTHESIS METHOD

BACKGROUND OF THE INVENTION

The present invention relates to 9-[2-(R)-[[Bis [[(isopropoxycarbonyl) oxy]methoxy]phosphinoyl] methoxy]propyl]adenine ("bis(POC)PMPA"), and compositions suitable for oral delivery of (R)-9-[2-(phosphonomethoxy) propyl]adenine ("PMPA") to a human or animal for use as an antiviral agent.

Phosphonomethoxy nucleotide analogs are known and various technologies for oral delivery are known. See, e.g., U.S. application Ser. No. 08/686,838, U.S. Pat. Nos. 5,208,221, 5,124,051, WO 91/19721, WO 94/03467, WO 94/03466, WO 92/13869, DE 41 38 584 A1, WO 94/10539, WO 94/10467, WO 96/18605, WO 95/07920, WO 95 79/07919, WO 92/09611, WO 92/01698, WO 91/19721, WO 88/05438, EP 0 632 048, EP 0 481 214, EP 0 369 409, EP 0 269 947, U.S. Pat. Nos. 3,524,846 and 5,386,030, Engel Chem. Rev. 77:349–367 1977, Farquhar et al., J. Pharm. Sci. 72:324–325 1983, Starrett et al., Antiviral Res. 19:267–273 1992, Safadi et al., Pharmaceutical Research 10(9):1350–1355 1993, Sakamoto et al., Chem. Pharm. Bull. 32(6):2241–2248 1984, and Davidsen et al., J. Med. Chem. 37(26):4423–4429 1994.

SUMMARY OF THE INVENTION

The invention provides a composition of formula (1), which includes 9-[2-(R)-[[bis[[(isopropoxycarbonyl)oxy] methoxy]phosphinoyl]methoxy]propyl]adenine.fumaric acid (1:1) ("bis(POC)PMPA fumarate" or "BPPF"),

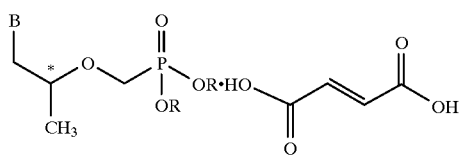

(1)

wherein B is adenin-9-yl and R independently is —H or —CH$_2$—O—C(O)—O—CH(CH$_3$)$_2$, but at least one R is —CH$_2$—O—C(O)—O—CH(CH$_3$)$_2$.

Other embodiments of the invention comprise orally administering to a patient infected with virus or at risk for viral infection a therapeutically effective amount of a composition of formula (1).

In another embodiment, a method for preparing a compound of formula (1) comprises contacting fumaric acid with bis(POC)PMPA.

Other embodiments include contacting lithium alkoxide and a 9-(2-hydroxypropyl)adenine solution.

A particular embodiment includes a composition comprising an (R,S)-PMPA solution at a pH of about 2.7–3.5 wherein the solution has less than about 0.1 g/mL (R,S)-PMPA and wherein about 90–94% of the PMPA is in the (R) configuration.

BRIEF DESCRIPTION OF THE FIGURES

FIGS. 4–7 are copies of the photographs made at a 132% enlargement.

DETAILED DESCRIPTION OF THE INVENTION

Figure 1:
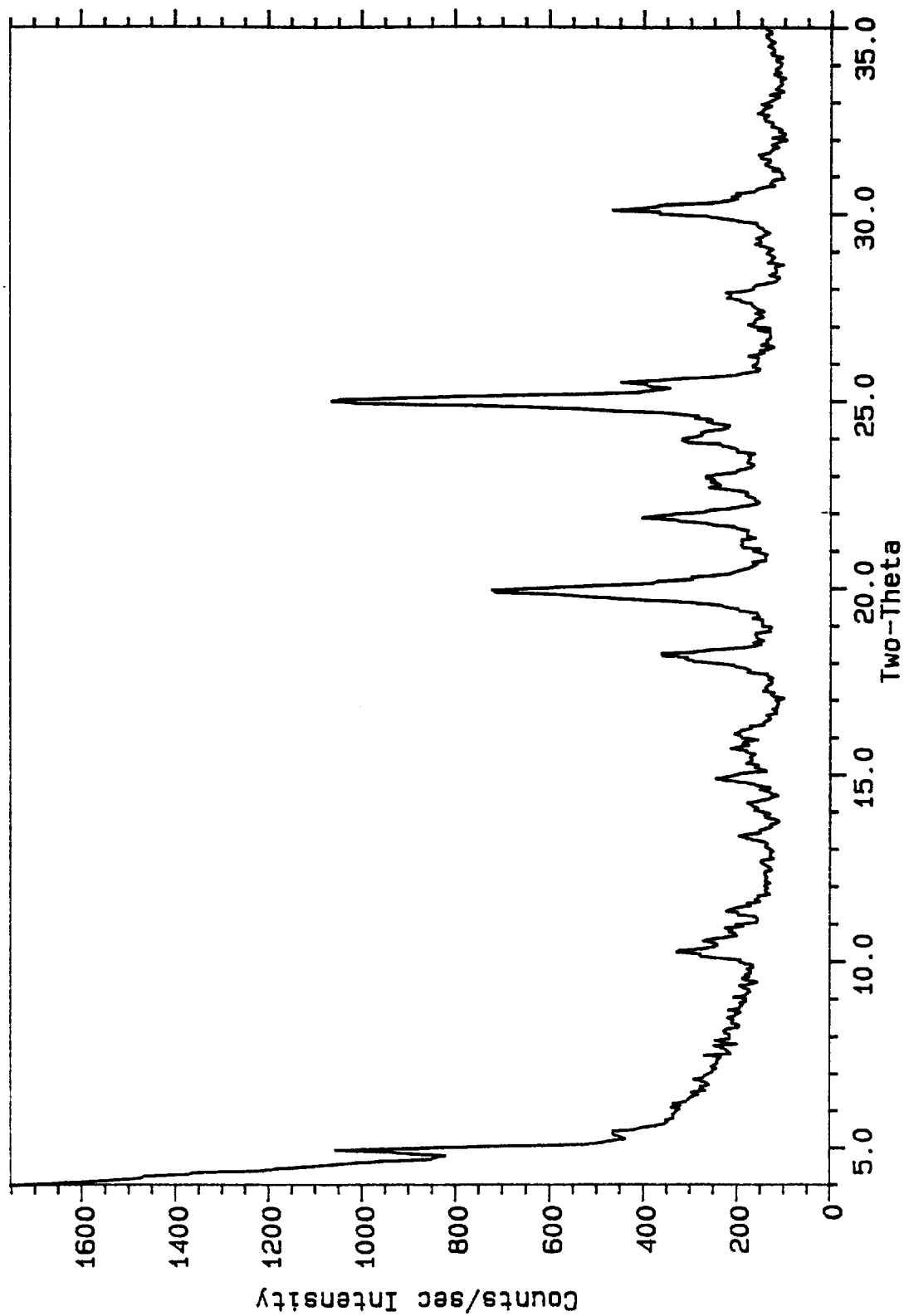
FIG. 1 shows a BPPF crystal X-ray powder diffraction pattern.
Figure 2:
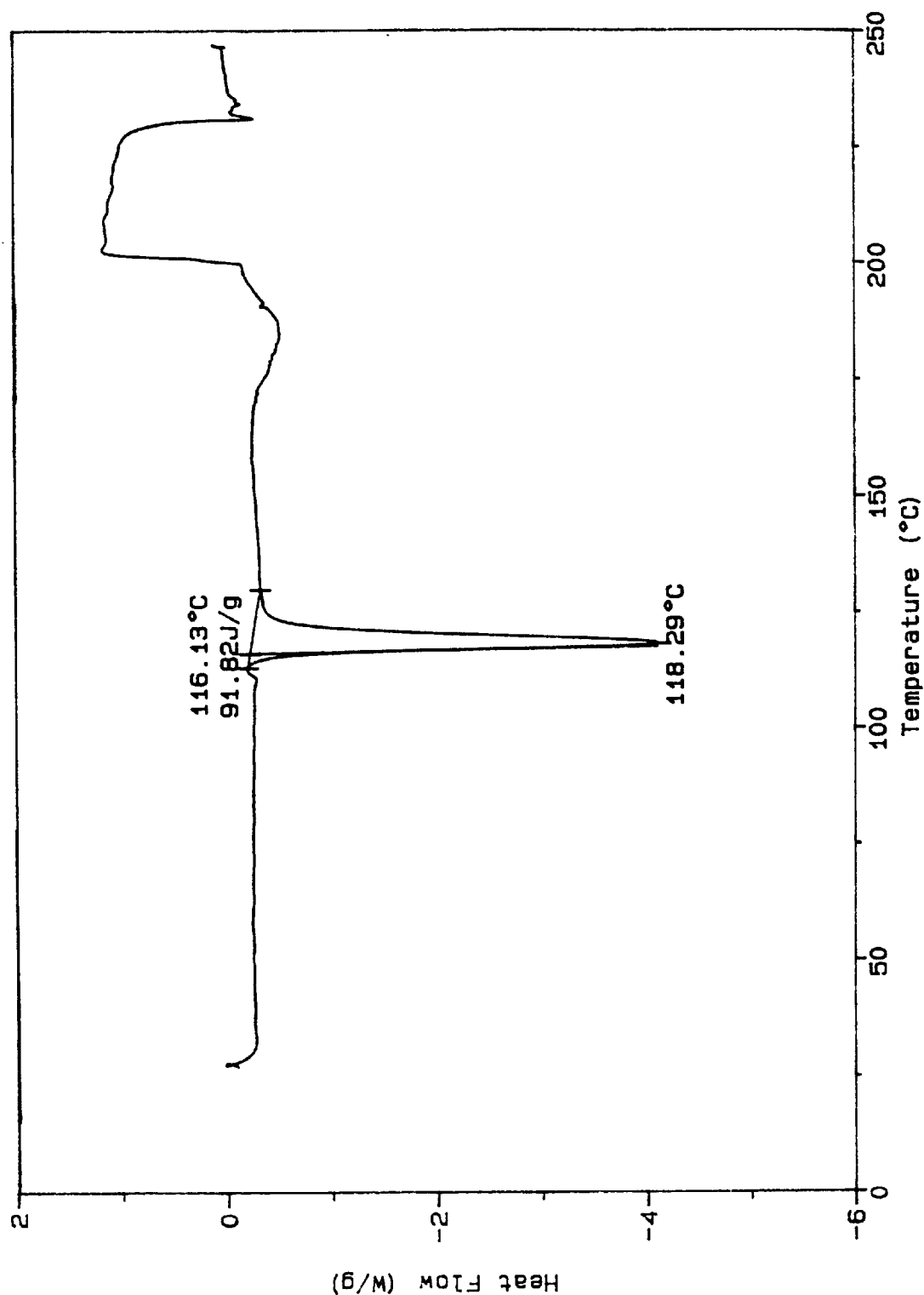
FIG. 2 shows a thermogram obtained by differential scanning calorimetry of BPPF crystals.
Figure 3:
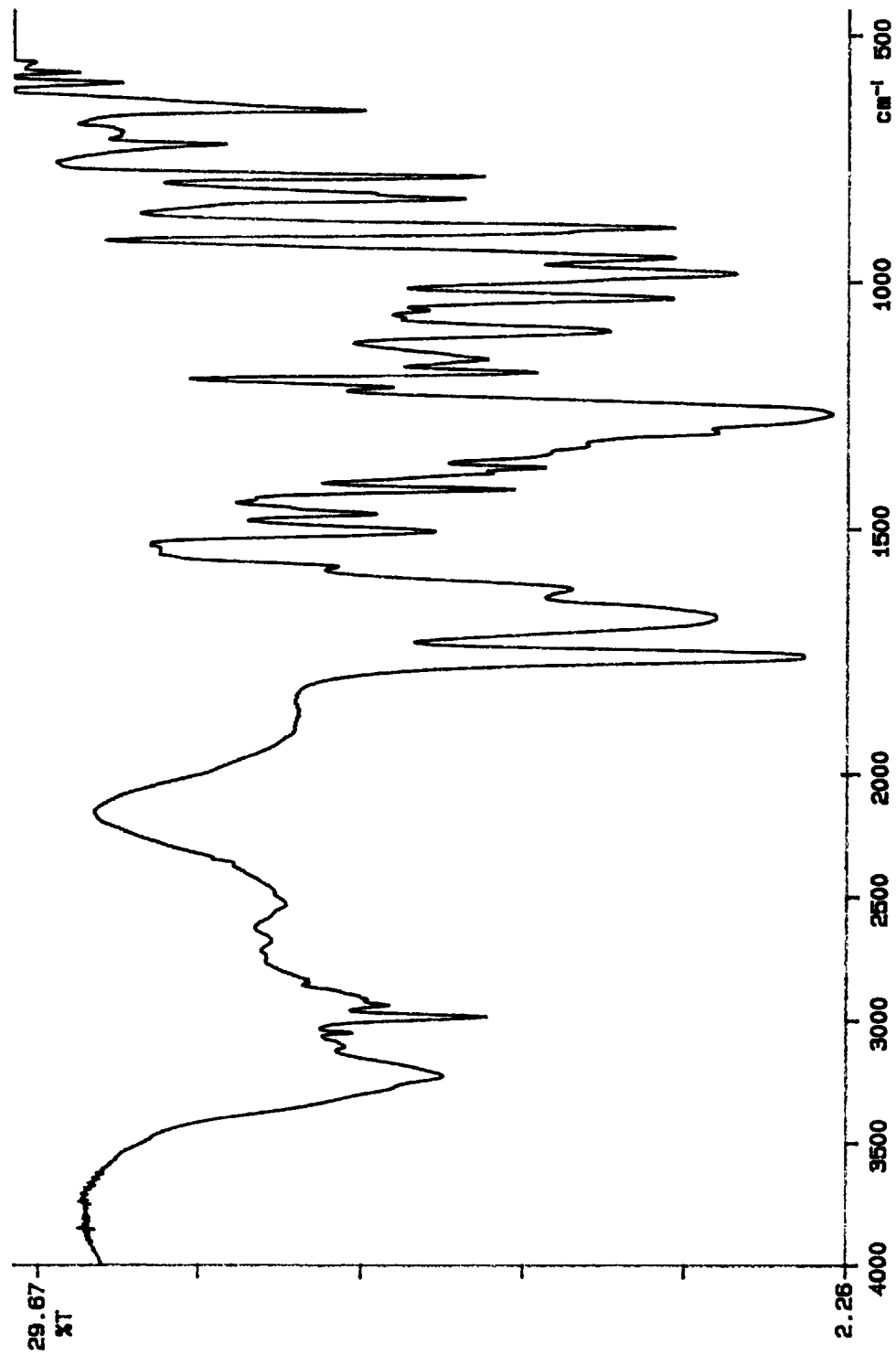
FIG. 3 shows a Fourier transform infrared absorption spectrum of BPPF crystals.

"Alkyl" as used herein, unless stated to the contrary, is a hydrocarbon containing 1, 2, 3, 4, 5, 6, 7, 8, 9, 10, 11 or 12 normal, secondary, tertiary or cyclic structures. Examples are —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$) CH$_2$CH$_3$, —C(CH$_3$)$_3$, —CH$_2$CH$_2$CH$_2$CH$_2$CH$_3$, —CH (CH$_3$)CH$_2$CH$_2$CH$_3$, —CH(CH$_2$CH$_3$)$_2$, —C(CH$_3$)$_2$CH$_2$CH$_3$, —CH(CH$_3$)CH(CH$_3$)$_2$, —CH$_2$CH$_2$CH(CH$_3$)$_2$, —CH$_2$CH (CH$_3$)CH$_2$CH$_3$, —CH$_2$CH$_2$CH$_2$CH$_2$CH$_3$, —CH(CH$_3$) CH$_2$CH$_2$CH$_2$CH$_3$, —CH(CH$_2$CH$_3$)(CH$_2$CH$_2$CH$_3$), —C(CH$_3$)$_2$CH$_2$CH$_2$CH$_3$, —CH(CH$_3$)CH(CH$_3$)CH$_2$CH$_3$, —CH(CH$_3$)CH$_2$CH(CH$_3$)$_2$, —C(CH$_3$)(CH$_2$CH$_3$)$_2$, —CH (CH$_2$CH$_3$)CH(CH$_3$)$_2$, —C(CH$_3$)$_2$CH(CH$_3$)$_2$, —CH(CH$_3$)C (CH$_3$)$_3$, cyclopropyl, cyclobutyl, cyclopropylmethyl, cyclopentyl, cyclobutylmethyl, 1-cyclopropyl-1-ethyl, 2-cyclopropyl-1-ethyl, cyclohexyl, cyclopentylmethyl, 1-cyclobutyl-1-ethyl, 2-cyclobutyl-1-ethyl, 1-cyclopropyl-1-propyl, 2-cyclopropyl-1-propyl, 3-cyclopropyl-1-propyl, 2-cyclopropyl-2-propyl, and 1-cyclopropyl-2-propyl.

"Alkoxide" as used herein, unless stated to the contrary, is a hydrocarbon containing 1, 2, 3, 4, 5 or 6 carbon atoms, as defined herein for alkyl, linked to an oxygen atom. Examples are —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$, —OCH(CH$_3$)CH$_2$CH$_3$, —OC(CH$_3$)$_3$, —OCH$_2$CH$_2$CH$_2$CH$_2$CH$_3$, —OCH(CH$_3$)CH$_2$CH$_2$CH$_3$, —OCH(CH$_2$CH$_3$)$_2$, —OC(CH$_3$)$_2$CH$_2$CH$_3$, —OCH(CH$_3$) CH(CH$_3$)$_2$, —OCH$_2$CH$_2$CH(CH$_3$)$_2$, —OCH$_2$CH(CH$_3$) CH$_2$CH$_3$, —OCH$_2$C(CH$_3$)$_3$, —OCH(CH$_3$)(CH$_2$)$_3$CH$_3$, —OC(CH$_3$)$_2$(CH$_2$)$_2$CH$_3$, —OCH(C$_2$H$_5$)(CH$_2$)$_2$CH$_3$, —O(CH$_2$)$_3$CH(CH$_3$)$_2$, —O(CH$_2$)$_2$C(CH$_3$)$_3$, —OCH$_2$CH (CH$_3$)(CH$_2$)$_2$CH$_3$, and —OCH$_2$CH$_2$CH$_2$CH$_2$CH$_2$CH$_3$.

Unless specified otherwise explicitly or by context, we express percentage amounts as % by weight (w/w). Thus, a BPPF preparation containing less than 1% water is a preparation containing less than 1% w/w water.

As used herein, and unless otherwise stated, whenever we provide a list of substituents, for example methoxide, ethoxide, n-propoxide, i-propoxide or t-butoxide to define a variable or component, such as an alkoxide for example, the variable or component is expressly meant to include any and all possible combinations of the listed substituents, e.g., alkoxide means methoxide, ethoxide or n-propoxide and alkoxide means i-propoxide or t-butoxide. Similarly, a list of organic solutions defined as comprising 1-methyl-2-pyrrolidinone, a trialkylamine (C$_{1-3}$ alkyl), methyl acetate, ethyl acetate, propyl acetate, isopropyl acetate, a C$_{1-6}$ alkanol, pyridine, acetone, toluene, CH$_2$Cl$_2$, dimethylformamide, dimethylsulfoxide, tetrahydrofuran, acetonitrile or a xylene may exclude acetone, xylenes or both from the list. Thus, we expressly intend that a given list of substituents defining a variable or component will include or exclude any combination of the substituents in the list, provided that not all possible substituents are omitted and the defined variable is eliminated, unless a given definition states that a variable or component may be absent.

The invention compounds are optionally enriched or resolved at the carbon atom chiral center (*) in accordance with prior findings associating optimal antiviral activity with the (R) configuration at this site. The chiral center at the carbon atom indicated by (*) is optionally in the (R) or (S) configuration, and can be enriched or found in substantially equal proportions. Typically the methyl group linked to the chiral center (*) in PMPA and bis(POC)PMPA will be in (R) configuration. Complexes of this invention include tautomeric forms of constituent components regardless of the manner in which they are depicted.

Formula (1) compounds may comprise BPPF with small amounts, typically less than 3%, usually less than 1% of mono(POM)PMPA, i.e., formula (1) compounds where one R is —H and the other R is —$CH_2$—O—C(O)—O—CH($CH_3$)$_2$.

Physical and Chemical Properties of bis(POC) PMPA fumarate

Crystalline BPPF has an unexpectedly superior combination of physico-chemical properties compared to the free base and other salts. Crystalline BPPF has a high melting point, is non-hygroscopic, has excellent solid state stability, and good aqueous solubility and stability. These properties are useful for manufacturing or for contributing to excellent oral bioavailability properties in humans and animals. These properties permit efficient delivery of BPPF or PMPA to biological fluids such as plasma or cell cytoplasm. For example, the oral bioavailability of 75 mg of crystalline BPPF administered once per day is about 30–40% in humans.

BPPF may or may not be in crystalline form. We have obtained a crystalline form of BPPF ("cBPPF") that we characterize by several methods, including X-ray powder diffraction and melting point. Workers commonly use X-ray powder diffraction to characterize or identify crystal compositions (see, e.g., U.S. Pharmacopoeia, volume 23, 1995, method 941, p 1843–1845, U.S.P. Pharmacopeial Convention, Inc, Rockville, Md.; Stout et al, *X-Ray Structure Determination; A Practical Gutide*, MacMillan Co., New York, N.Y. 1968). The diffraction pattern obtained from a crystalline compound is often diagnostic for a given crystal form, although weak or very weak diffraction peaks may not always appear in replicate diffraction patterns obtained from successive batches of crystals. This is particularly the case if other crystal compositions are present in the sample in appreciable amounts. The relative intensities of bands, particularly at low angle X-ray incidence values (low 2θ) may vary due to preferred orientation effects, direction of crystal growth, particle size and other conditions of measurement. Thus, the relative intensities of the diffraction peaks are not conclusively diagnostic of the crystal form in question. Instead, one should look to the position of the peaks optionally including their relative spacing and general pattern, rather than their precise amplitude to determine the identity of BPPF crystals. Moreover, it is not necessary to rely for identification on all bands that one observes in a highly purified reference sample; even a single band may be diagnostic of a given crystal form, e.g., 25.0 for cBPPF.

Additional diagnostic techniques that one can optionally use to identify crystalline BPPF include differential scanning calorimetry (DSC) and infrared absorption spectroscopy (IR). DSC measures thermal absorption transition temperatures at which a crystal absorbs heat when its crystal structure changes. DSC provides an alternate means for one to distinguish between different crystal compositions based on their different absorption temperatures. IR measures absorption of infrared light caused by the presence of particular chemical bonds associated with groups in a molecule that vibrate in response to the light. DSC and/or IR can thus provide physical information one can use to describe BPPF crystals.

The cBPPF x-ray powder diffraction pattern usually shows a peak(s) at about 25.0, typically at about 25.0 and about 20.0, or more typically at about 25.0, about 20.0 and about 30.1 and ordinarily at least at about 25.0, about 20.0, about 30.1 and about 21.9. The cBPPF spectrum commonly has peaks at about 4.9, about 10.2, about 10.5, about 18.2, about 20.0, about 21.9, about 24.0, about 25.0, about 25.5, about 27.8, about 30.1 and about 30.4. The cBPPF x-ray powder diffraction pattern usually shows a peak(s) at any one (or combination) of about 20.0 and/or 21.9 and/or 25.0 and/or 30.1.

cBPPF crystals exhibit a DSC absorption peak at about 118° C. with an onset at about 116° C. and an IR spectrum showing characteristic bands expressed in reciprocal centimeters at approximately 3224, 3107–3052, 2986–2939, 1759, 1678, 1620, 1269 and 1102. Different cBPPF crystal preparations have a bulk density of about 0.15–0.30 g/mL, usually about 0.2–0.25 g/mL. They typically are essentially free of solvent, containing less than 1% solvents if adequately recovered from the crystallization bath, and generally do not contain detectable lattice-entrained solvent molecules.

BPPF crystals are typically anhydrous and non-hygroscopic, containing little or no detectable water. In general, BPPF crystals ordinarily will contain less than about 1%, typically less than about 0.5% water. Moreover, BPPF crystals ordinarily will contain less than about 10%, typically will contain less than about 5%, often less than about 1%, and usually less than about 0.5% amorphous BPPF.

Figure 4:
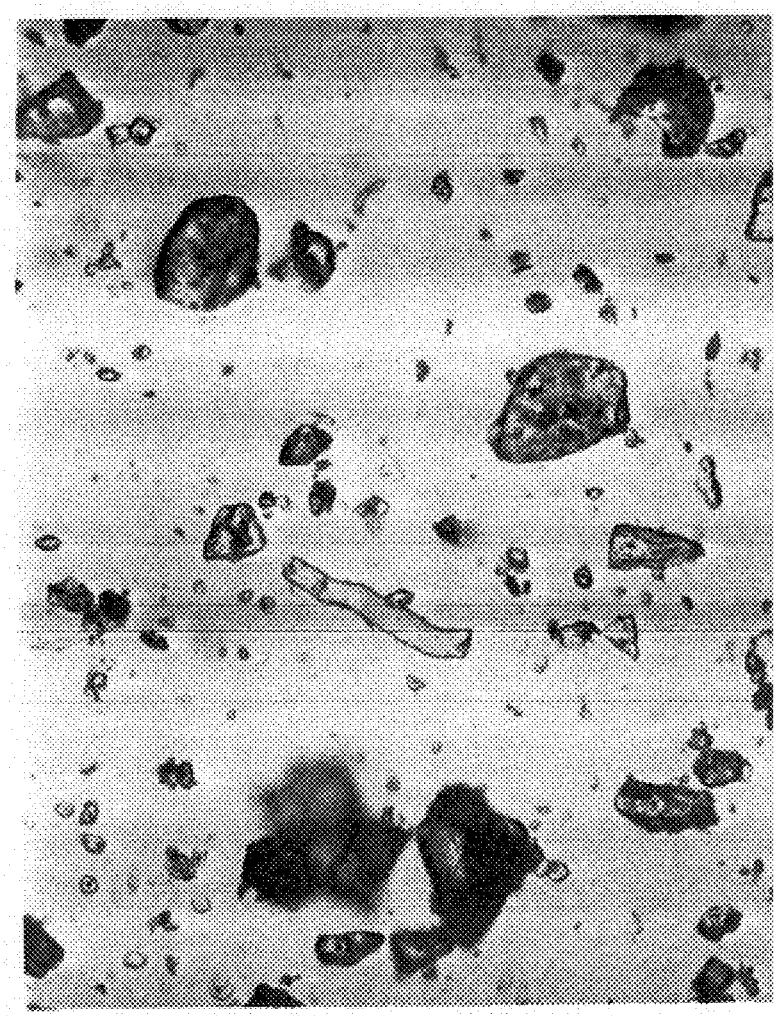
FIG. 4 is a picture of a photograph showing embodiments of BPPF crystals at 100× magnification by light microscopy.
Figure 5:
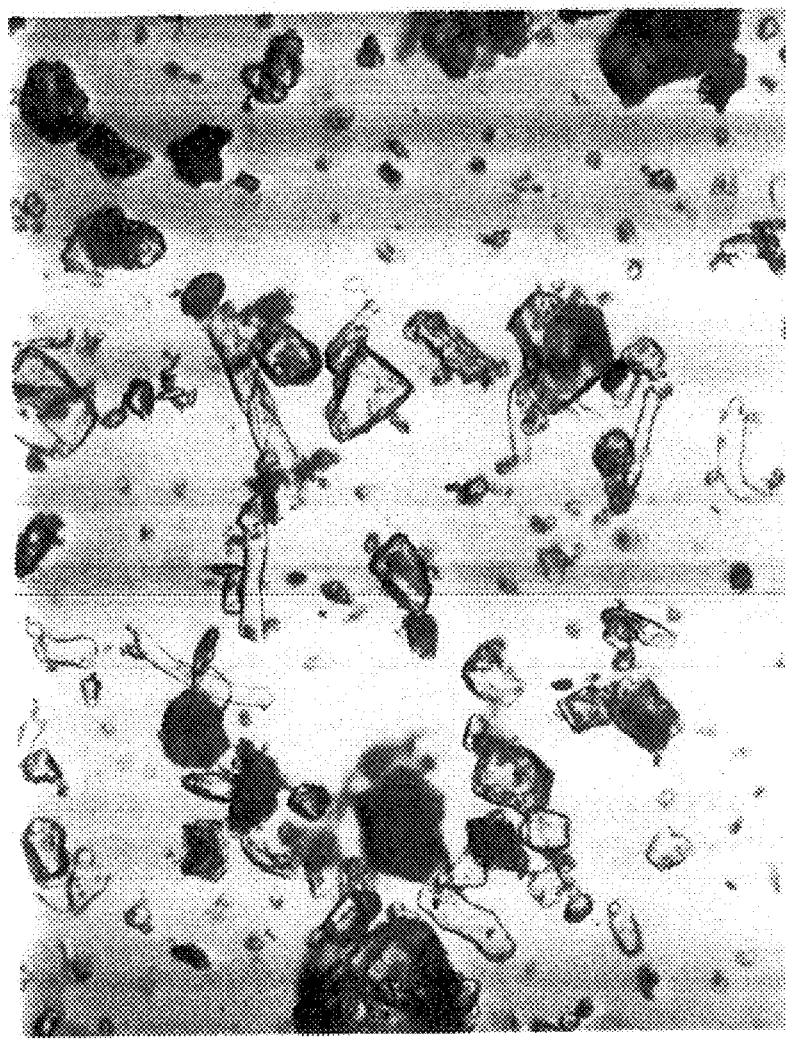
FIG. 5 is a picture of a photograph showing embodiments of BPPF crystals at 100× magnification by light microscopy.
Figure 6:
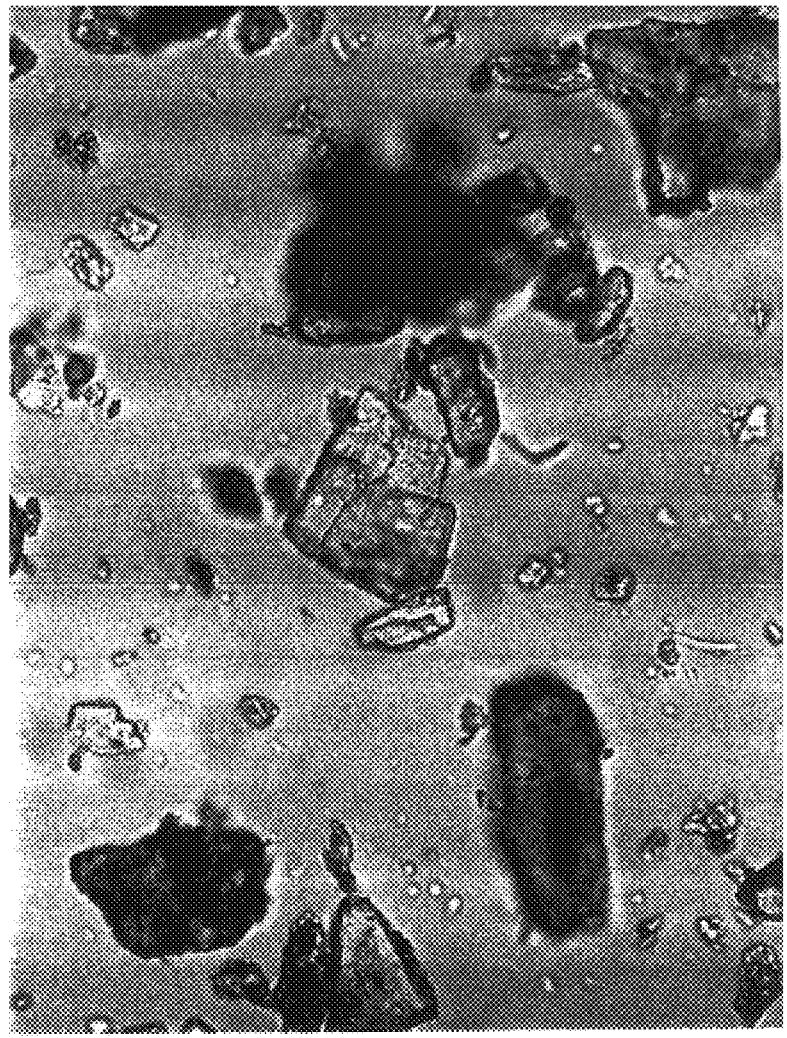
FIG. 6 is a picture of a photograph showing embodiments of BPPF crystals at 200× magnification by light microscopy.
Figure 7:
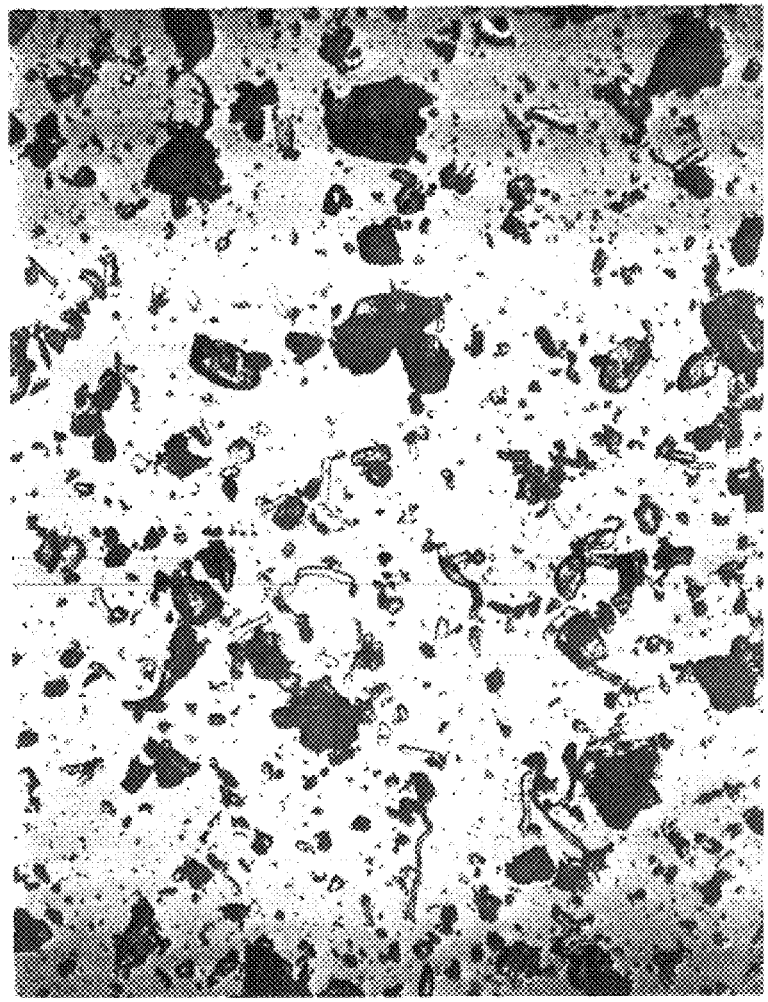
FIG. 7 is a picture of a photograph showing embodiments of BPPF crystals at 40× magnification by light microscopy.

BPPF crystals usually appear as an opaque white or off-white crystalline powder when dry. The crystals obtained from a given preparation are usually polydisperse in size and have a range of shapes including needles, plates, irregular tablets and aggregates of needles, plates or tablets. BPPF crystals typically range in size along their longest dimension from about 1 μm to about 500 μm, typically about 5–170 μm, usually about 10–110 μm, along the largest dimension of most of the individual crystals in a given preparation. These crystals may have fractured or angular edges. Photographs in FIGS. 4–7 show cBPPF having various shapes, including tablets, rods, needles, plates and aggregates.

Utilities

PMPA and bis(POC)PMPA are known to be useful in the treatment or prophylaxis of one or more viral infections in man or animals, including particularly retroviruses, HIV, SIV and GALV, and hepadnaviruses, e.g., HBV. Other infections to be treated with PMPA include MSV, RSV, FIV, MuLV, and other retroviral infections of rodents and other animals. The prior art describes the antiviral specificity of PMPA and the invention compounds share this specificity.

Dosages and suitable administration routes to best attack the site of infection are well known in the art for PMPA. Determination of proper doses of BPPF is a straightforward matter for the clinician, taking into account the molecular weight of the complexes of this invention and, when administering them orally, their bioavailability in animals or as deduced in clinical trials with humans, as well as other factors well-known to the artisan.

Invention compositions that comprise BPPF are administered by any route appropriate to the condition to be treated, suitable routes including oral, rectal, nasal, pulmonary, topical (including transdermal, ocular, buccal and sublingual), vaginal and parenteral (including subcutaneous, intramuscular, intravenous, intradermal, intrathecal and epidural). Generally, the invention compositions are administered orally, but compositions containing BPPF can be administered by any of the other routes noted above. Oral dosages of the compounds of this invention in humans for antiviral therapy will range about from 0.01 to 20 mg/Kg/day, typically about from 0.3 to 5 mg/Kg/day. Oral administration of tablets containing 75 mg cBPPF once per day to humans resulted in oral bioavailability of PMPA on day 1 of about 17–38% in fasted persons and of about 27–60% in fed persons.

While it is possible for BPPF to be administered as a pure compound it is preferable to present it as a pharmaceutical formulation. The formulations of the present invention comprise BPPF, together with one or more pharmaceutically acceptable excipients or carriers ("acceptable excipients") and optionally other therapeutic ingredients. The carrier(s) must be "acceptable" in the sense of being compatible with the other ingredients of the formulation and not deleterious to the patient.

The formulations include those suitable for topical or systemic administration, including oral, rectal, transdermal, pulmonary, nasal, buccal, sublingual, vaginal or parenteral (including subcutaneous, intramuscular, intravenous, intradermal, intrathecal and epidural) administration. The formulations are in unit dosage form and are prepared by any of the methods well known in the art of pharmacy. Such methods include the step of bringing into association the active ingredient with the carrier or excipient which constitutes one or more accessory ingredients. In general the formulations are prepared by uniformly and intimately bringing into association the active ingredient with liquid carriers or finely divided solid carriers or both, and then, if necessary, drying or shaping the product.

Formulations of the present invention suitable for oral administration may be presented as discrete units such as sachets, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, typically with one or more accessory ingredients or excipients. Tablets will typically comprise about 10–300 mg of BPPF per tablet, usually about 10–100 mg, e.g., about 75 mg. Usually the BPPF is present in solid formulations as cBPPF. Compressed tablets may be prepared by compressing in a suitable machine BPPF in a free-flowing form such as a powder or granules, optionally mixed with a binder, lubricant, inert diluent, surface active or dispersing agent. Molded tablets may be made by molding in a suitable machine a mixture of powdered BPPF moistened with a liquid diluent, typically an inert diluent. The tablets may optionally be coated and painted, embossed, or scored and may be formulated to provide slow or controlled release of the active ingredient therein. Typical tablet ingredients include one or more binders, diluents, disintegrants or lubricants, which facilitate tablet manufacture or tablet disintegration after ingestion. The tablets are optionally made by wet granulation of one or more excipients with BPPF, drying and milling. A binder such as pregelatinized starch is optionally present at a level of about 1–10%. A disintegrant such as cross-linked cellulose is optionally present at a level of about 0.5–5% to facilitate tablet dissolution. A diluent such as a monosaccharide or disaccharide is optionally present at a level of about 50–60% to mask the physical properties of BPPF or to facilitate tablet dissolution. A lubricant is optionally present at a level of about 0.25–5% to facilitate tablet ejection during manufacture. Embodiments include a product made by the process of compressing a mixture containing BPPF and an acceptable excipient.

For infections of the eye or other external tissues, e.g. mouth and skin, the formulations are preferably applied as a topical ointment or cream containing the active ingredient (s) in an amount of, for example, 0.01 to 10% w/w (including active ingredient(s) in a range between 0.1% and 5% in increments of 0.1% w/w such as 0.6% w/w, 0.7% w/w, etc), preferably 0.2 to 3% w/w and most preferably 0.5 to 2% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the wax together with the oil and fat make up the emulsifying ointment base which forms the oily dispersed phase of the cream formulations.

Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is suitably present in such formulations in a concentration of 0.01 to 20%, in some embodiments 0.1 to 10%, and in others about 1.0% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal or inhalational administration wherein the carrier is a solid include a powder having a particle size for example in the range 1 to 500 microns (including particle sizes in a range between 20 and 500 microns in increments of 5 microns such as 30 microns, 35 microns, etc). Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Inhalational therapy is readily administered by metered dose inhalers.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration are sterile and include aqueous and non-aqueous injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as recited above, or an appropriate fraction thereof, of BPPF.

In addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor.

Veterinary carriers are materials useful for the purpose of administering the composition to cats, dogs, horses, rabbits and other animals and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing a matrix or absorbent material and as active ingredient one or more compounds of the invention in which the release of the active ingredient can be controlled and regulated to allow less frequent dosing or to improve the pharmacokinetic or toxicity profile of the compound. Controlled release formulations adapted for oral administration in which discrete units comprising BPPF can be prepared according to conventional methods.

Synthetic Methods

BPPF is prepared by forming a complex or salt between fumaric acid and PMPA. PMPA is a known compound prepared by known methods or by the following procedure.

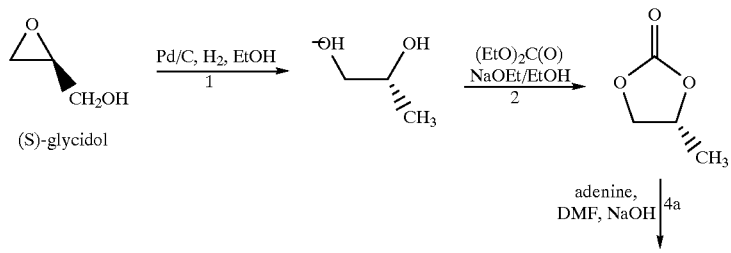

-continued

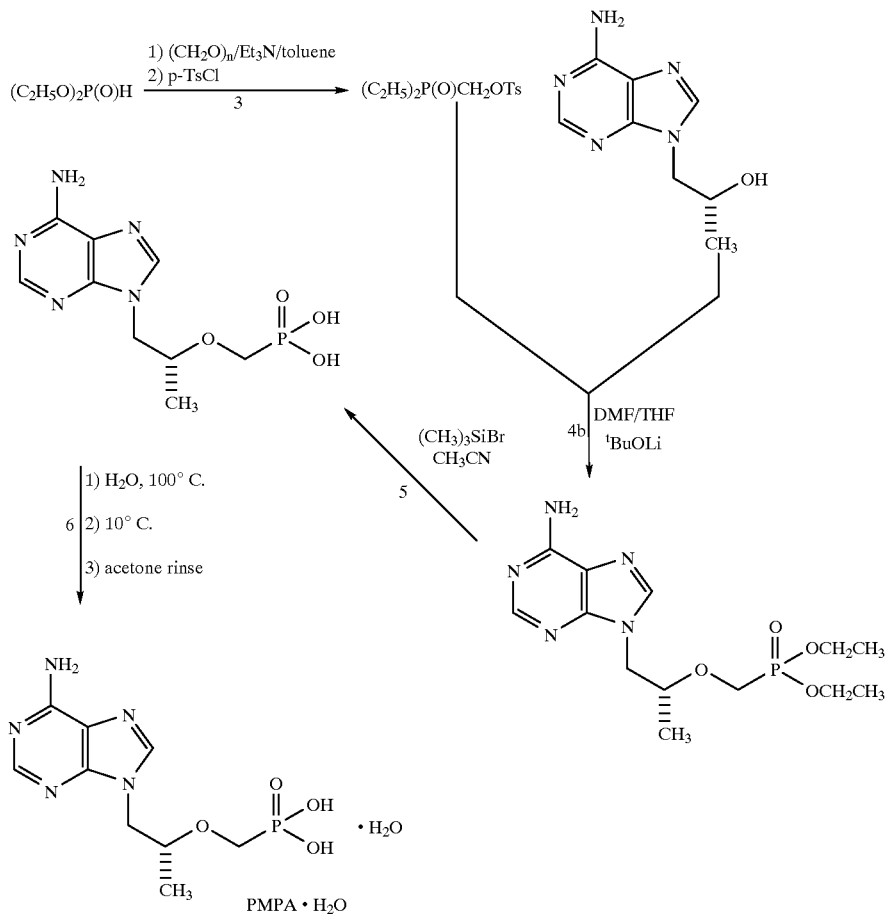

BPPF Synthesis

PMPA is esterified using $(CH_3)_2CHOC(O)CH_2Cl$ and complexed with fumaric acid using the following method.

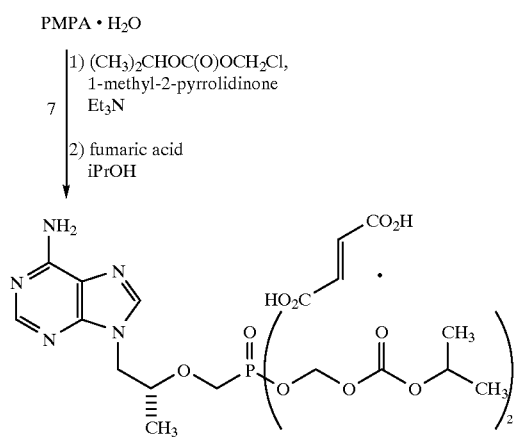

Process Summary

In the PMPA preparative method: (S)-Glycidol is reduced to (R)-1,2-propanediol by catalytic hydrogenation, which is then reacted with diethyl carbonate to afford (R)-1,2-propylene carbonate. The carbonate is reacted with adenine and catalytic amounts of a base such as sodium hydroxide to give (R)-9-[2-(diethylphosphonomethoxy)propyl]adenine which, without isolation, is reacted with lithium alkoxide and diethyl p-toluenesulfonyloxymethylphosphonate (prepared by reacting diethyl phosphite and paraformaldehyde, and tosylating the product in situ). The resulting (R)-9-[2-diethylphosphonomethoxypropyl] adenine is deesterified with bromotrimethylsilane to give crude PMPA, which is then purified by precipitation from water with pH adjustment. The product is further purified by recrystallization with water to afford PMPA monohydrate.

The process uses a small amount of a base such as NaOH at step 1, which increases the reaction rate about 10-fold compared to the same reaction lacking the base. Step 1 also uses hydrogen gas instead of using a reagent such as $HCO_2NH_4$ to generate hydrogen in situ. The process uses lithium alkoxide at step 4b, which is mildly exothermic on addition to the reaction mixture. The use of a highly reactive base such as NaH, results in an exothermic reaction that generates hydrogen gas in a reaction that is difficult to control. The use of NaH thus requires more labor and care to use than lithium alkoxide. Lithium alkoxide bases also give a product that has an improved by-product profile compared to that obtained using NaH, e.g., lower amounts of starting material or overalkylated products usually result from the use of lithium alkoxide.

The scheme and process steps depict synthesis of (R)-PMPA and (R)-bis(POC)PMPA. One can practice the method using chirally impure starting materials such as (R,S)-glycidol to obtain a chiral mixture of intermediates, e.g., a chiral mixture of 1,2-propylene carbonate, PMPA or bis(POC)PMPA.

Step 1. (R)-1,2-Propanediol: (S)-Glycidol (1.0 kg, 13.5 moles) is added to a reactor containing (i) an inert, e.g., nitrogen, atmosphere and (ii) a stirred suspension of 5% palladium on activated carbon (50% wet) catalyst (100 g) in denatured ethyl alcohol containing 2 mole % sodium hydroxide (7.85 kg EtOH and 54 g of 16.7% NaOH solution). The contents of the inerted reactor containing catalyst and the ethanol solution is usually cooled to about 0° C. (usually about −5 to 5° C.) before the (S)-glycidol is added. Hydrogen gas at no more than 20 psi is then introduced to the inerted reaction vessel containing reactants at a temperature of no more than 25° C. The mixture is agitated for approximately 4–5 hours, until hydrogen consumption stops. Reaction completion is monitored by TLC (trace or no (S)-glycidol remaining). The mixture is then filtered e.g., diatomaceous earth (about 150 g), to remove solids and the filtrate, at no more than 50° C., is concentrated in vactio, until volatile collection stops or is very slow, to obtain an oil containing the crude product. The crude product is used directly in the next step. Title compound yield is about 100%.

Step 2. (R)-1,2-Propylene carbonate: Diethyl carbonate (1.78 kg, 15.1 moles) and sodium ethoxide in denatured ethyl alcohol (210 g of 21% w/w sodium ethoxide in ethanol) are added to (R)-1,2-propanediol (1.0 kg theoretical based on the quantity of (S)-glycidol used in step 1 above), and the solution is heated to 80 to 150° C. to distill off the ethanol. If necessary to achieve reaction completion, additional diethyl carbonate (0.16 kg) is added to the reaction mixture, followed by distillation to remove ethanol. Reaction completion is monitored by TLC showing a trace or no detectable (R)-1,2-propanediol. The residue is fractionally distilled at 120° C. and 10–17 mm Hg, to yield the title compound as a colorless liquid. The product purity is typically 96% or greater purity by GC analysis.

Step 3. Diethyl p-toluenesulfonyloxymethylphosphonate: In a reactor containing an inert atmosphere, e.g., nitrogen, a mixture of diethyl phosphite (0.80 kg), paraformaldehyde (0.22 kg), and triethylamine (0.06 kg) in toluene (0.11 kg) is heated at 87° C. for about 2 hours, then refluxed for about 1 hour, until the reaction is complete as monitored by TLC showing a trace or no detectable diethyl phosphite. During the reaction, the inert atmosphere is maintained. Toluene is used to moderate the reaction, which may otherwise run out of control. Reaction completion is optionally confirmed by $^1$H NMR (diethyl phosphite peak at δ8.4–8.6 ppm no longer detected). The solution is cooled to about 1° C. (typically about −2 to 4° C.) and p-toluenesulfonyl chloride (1.0 kg) is added and then triethylamine (0.82 kg) at about 5° C. is slowly added (exothermic addition) while maintaining the temperature at no more than about 10° C. (typically 0 to 10° C.). The resulting mixture is warmed to 22° C. and stirred for at least about 5 hours (typically about 4.5 to 6.0 hours), until the reaction is complete as shown by TLC (trace or no p-toluenesulfonyl chloride detectable) and optionally confirmed by $^1$H NMR (p-toluenesulfonyl chloride doublet at δ7.9 ppm no longer detected). The solids are removed by filtration and washed with toluene (0.34 kg). The combined washings and filtrate are washed either twice with water (1.15 kg per wash), or optionally with a sequence of water (1.15 kg), 5% aqueous sodium carbonate (3.38 kg), and then twice with water (1.15 kg per wash). After each wash, the reactor contents are briefly agitated, allowed to settle and the lower aqueous layer is discarded. If the reaction results in an emulsion, brine (0.23 kg of water containing 0.08 kg NaCl) may be added to the first organic/water mixture, followed by agitating the reactor contents, allowing the solids to settle, discarding the lower aqueous layer, adding 1.15 kg water, agitating, allowing solids to settle and again discarding the lower aqueous layer. The organic phase, which is at no more than 50° C., is distilled in vacuo (to LOD at 110° C. of no more than 10% and water content, by KF titration, no more than 0.3%), affording a yield of about 60–70% of the title compound as an oil of about 85–95% purity, exclusive of toluene.

Step 4. (R)-9-[2-(Diethylphosphonomethoxy)propyl] adenine: This compound is prepared using a composition comprising lithium alkoxide and 9-(2-hydroxypropyl) adenine. One will contact 9-(2-hydroxypropyl)adenine and lithium alkoxide during the synthesis, typically at a temperature of about 0–50°, usually about 20–45°. The 9-(2-hydroxypropyl)adenine in these compositions and methods is typically present in an organic solution. The organic solution typically comprises an organic solvent such as dimethylformamide, tetrahydrofuran, toluene, acetonitrile, $CH_2Cl_2$ or a $C_{1-6}$ alkanol, usually dimethylformamide or toluene. These compositions optionally further comprise p-toluenesulfonyloxymethylphosphonate or adenine, which, if present are at low levels, typically less than about 15% compared to 9-(2-hydroxypropyl) adenine, usually less than about 10%. These compositions and methods typically use lithium t-butoxide or lithium i-propoxide. They will generally also use about 0.9–3.0 molar equivalents (relative to adenine base used in step 4a), typically about 1.2–1.8, of p-toluenesulfonyloxymethylphosphonate as a reactant with lithium alkoxide and 9-(2-hydroxypropyl)adenine. Embodiments include a product produced by the process of contacting 9-(2-hydroxypropyl)adenine and lithium alkoxide. In these embodiments, the reactants are typically present in an organic solution that also contains p-toluenesulfonyloxymethylphosphonate.

In an embodiment, synthesis of (R)-9-[2-(diethylphosphonomethoxy)-propyl]adenine, shown in above as step 4, is described as follows. In a reactor containing an inert atmosphere, e.g., nitrogen, a mixture of adenine (1.0 kg), sodium hydroxide (11.8 g), (R)-1,2-propylene carbonate (0.83 kg), and N,N-dimethylformamide (6.5 kg) is heated to about 130° C. (typically about 125–138° C.) for about 18–30 hours until the reaction is complete as optionally monitored by area normalized HPLC showing no more than about 0.5% adenine remaining. The resulting mixture is cooled to about 25° C., typically about 20–30° C., and contains the stage I intermediate, (R)-9-(2-hydroxypropyl)adenine, which may precipitate out at this point. After cooling, lithium t-butoxide (3.62 kg), 2.0M in tetrahydrofuran is added to the stage I intermediate, to produce the lithium salt of (R)-9-(2-hydroxypropyl)adenine in a mildly exothermic addition. The slurry is treated with diethyl p-toluenesulfonyloxymethylphosphonate (1.19 kg) and the mixture is heated to a temperature of about 32° C., typically about 30–45° C., and is stirred for at least about 2 hours (typically about 2–3 hours) during which time the mixture becomes homogeneous. More diethyl p-toluenesulfonyloxymethylphosphonate (1.43 kg) is added and the mixture is stirred at a temperature of about 32° C. (typically about 30–45° C.) for at least about 2 hours (typically about 2–3 hours). Additional lithium t-butoxide (0.66 kg), 2.0M in tetrahydrofuran and diethyl p-toluenesulfonyloxymethylphosphonate (0.48 kg per addition) are added twice more, each time followed by stirring the mixture, which is at a temperature of about 32° C. for at least about 2 hours. Reaction completion is optionally monitored by area normalized HPLC showing no more than about 10% of stage I intermediate remaining. If the reaction is incomplete, additional lithium t-butoxide (0.33 kg), 2.0M in tetrahydrofuran and diethyl p-toluenesulfonyloxymethylphosphonate (0.24 kg) are added and the reaction mixture is maintained at a temperature of about 32° C. for at least about 2 hours to achieve reaction completion. The mixture is then cooled to about 25° C. (typically about 20–40°) and glacial acetic acid (0.5 kg) is then added. The resulting mixture is concentrated in vacuo at a final maximum mixture temperature of about 80° C. under about 29 in Hg vacuum. The residue is cooled to about 50° C. (typically about 40–60° C.) and water (1.8 kg) is added and the reaction is rinsed forward with additional water (1.8 kg). The solution is continuously extracted with dichloromethane (about 35 kg) for 12–48 hours with one addition of glacial acetic acid (0.2 kg) to the aqueous phase after about 5 hours and another addition after about 10 hours of continuous extraction time. Extraction completion is optionally confirmed by area normalized HPLC as shown by no more than about 7% of (R)-9-[2-(diethylphosphonomethoxy)propyl]adenine remaining in the aqueous phase. The combined dichloromethane extracts are concentrated initially at atmospheric pressure then in vacuo at an extract temperature of no more than about 80° C. to give the title compound as a viscous orange oil. The title compound yield is about 40–45% by weight normalized HPLC and its purity is typically 60–65% by area normalized HPLC. The actual weight of the title compound after concentration is approximately 1.6 times the theoretical weight. The additional observed weight is attributed to impurities and/or solvents remaining after the continuous extraction and concentration.

Step 5. (R)-9-[2-(Phosphonomethoxy)propyl]adenine, crude: Crude (R)-PMPA is prepared by converting (R)-PMPA diethyl ester to the free acid. The proportion of the (R)-isomer in a mixture comprising about 90–94% (R)-PMPA and about 6–10% (S)-PMPA may be increased to about 97–99% (R)-PMPA. The enrichment of the (R) isomer is accomplished by precipitating PMPA from a composition comprising (R,S)-PMPA at a pH of about 2.7–3.5 wherein the solution has less than about 0.1 g/mL, generally less than about 0.08 g/mL, typically less than about 0.07 g/mL, of (R,S)-PMPA wherein the (R,S)-PMPA solution is at a temperature of about 10–25° C., typically at about 15–22° C. Enrichment of the (R)-PMPA isomer in such (R,S)-PMPA solutions at about 40–55° C. may be accomplished by adjusting the pH to about 2.4–3.5, optionally followed by bringing the solution temperature to about 10–25° C. and then optionally adjusting the pH to about 2.7–3.5.

In an embodiment, synthesis of crude (R)-PMPA, shown in above as step 5, is described as follows. Bromotrimethylsilane (1.56 kg) is added to a reactor containing a mixture of crude (R)-9-[2-(diethylphosphonomethoxy)propyl]-adenine (1.0 kg calculated based on adenine input described in step 4 above) and acetonitrile (0.9 kg) with cooling to maintain a temperature no higher than about 50° C. The lines are rinsed forward with acetonitrile (0.3 kg) and the mixture is refluxed at about 60–75° C. for about 2–4 hours with moderate agitation to avoid splashing the reactor contents. Reaction completion is monitored by area normalized HPLC showing no more than about 3% total of monoethyl PMPA and diethyl PMPA remaining. If the reaction is incomplete, additional bromotrimethylsilane (0.04 kg) is charged into the reactor and the reaction is refluxed for at least about 1 hour with moderate agitation. The contents are heated to no higher than 70° to remove volatiles by distillation initially at atmospheric pressure and then in vacuo (about 24–27 in Hg) at no higher than about 70° C. The reactor contents are then cooled to about 20° C. (typically about 15–25° C.) and water (1.9 kg) is added (exothermic addition) to the residue with the temperature of the contents maintained at no higher than about 50° C. The mixture is cooled to 20° C. and washed with dichloromethane (1.7 kg) by agitating for about 30 minutes. The isolated aqueous phase is then filtered through a 1 μm cartridge filter, diluted with water (3.2 kg), heated to about 40° C. (typically about 35–50° C.) and adjusted to pH about 1.1 (typically about 0.9–1.3) with aqueous sodium hydroxide (about 0.15 kg NaOH as a 50% solution) while the temperature is maintained at about 45° C. PMPA seed crystals are added to the mixture and the pH is adjusted to about 2.8 (typically about 2.6–3.0) with a 50% aqueous sodium hydroxide solution (about 0.15 kg NaOH) while the temperature is maintained at about 45° C. (typically about 35–50° C.). The solution is cooled to about 22° C. (typically about 15–25° C.) over about 3–20 hours with slow to moderate agitation that avoids splashing the contents, during which time the product should precipitate, beginning at about 35° C. The pH of the slurry is adjusted to about 3.2 (typically about 3.1–3.3), usually using 50% aqueous sodium hydroxide or concentrated hydrochloric acid, if necessary. The slurry is cooled to approximately 5° C., typically about 0–10° C., and slowly agitated for at least about 3 hours in that temperature range. The solids are collected by filtration, washed sequentially with cold water (0.35 kg) and acetone (0.3 kg) giving crude PMPA as a damp solid typically of about 97% purity. The product is heated to about 50° C. and dried in vacuo to a water content of less than 10%. The quantity of diethyl PMPA is calculated from the quantity of adenine used in the preceding step of the synthesis (assuming 100% yield) and not from the net weight of the crude diethyl PMPA, which may contain other compounds.

Step 6. (R)-9-[2-(Phosphonomethoxy)propyl]adenine, pure: A suspension of the crude PMPA (1.00 kg corrected for water content) (Step 5 product) in water is heated to about 100° C. (typically about 95–110° C.) with moderate to high agitation until all solids dissolve, and the resulting solution is clarified by filtration while hot, rinsing forward using additional hot water (1 kg, about 95–110° C.). The filtrate is heated to 100° C. prior to cooling, first to about 30° C. (typically about 20–25° C.) over about 3–5 hours with slow agitation, then cooling is continued to about 10° C. (typically about 5–15° C.). After holding at about 10° C. for at least about 3 hours, the solids are collected by filtration and washed sequentially with cold water (1.5 kg, about 0–10° C.) and then acetone (1 kg). The wet cake is dried in vacuo at about 50° C. (typically about 40–60° C.) to a water content of about 5.9% (typically about 3.9–7.9%), affording pure PMPA monohydrate. The product purity is typically 98% or greater by both area normalized and weight normalized HPLC. If the chemical purity is unsatisfactory, the product may be repurified by a repeat of this step.

Optional recrystallization: PMPA (0.75 g) is recrystallized from $H_2O$ (11.3 mL, 15:1 wt. ratio) by heating the suspension to 95–100° C. Upon cooling to room temperature, the crystallized PMPA is chilled in a freezer. After 3 h the crystals are filtered on a coarse frit fit with Tyvek™, the filter cake rinsed with ice-cold $H_2O$ and acetone, and air dried to constant weight to give a fluffy white solid (Preparation B). Recovery is about 0.64 g (85.3%). HPLC typically shows 98.5–98.9% pure PMPA.

Preparation B PMPA is optionally recrystallized from 9.6 mL (15:1 wt. ratio) H$_2$O heated to 95–100° C. Upon cooling to room temperature, the crystallized PMPA is chilled in a freezer overnight. The PMPA is filtered through a coarse frit fit with Tyvek™ and the filter cake is rinsed with ice-cold H$_2$O and acetone, then sucked dry to constant weight to afford a fluffy, white solid (Preparation C). PMPA recovery is typically about 0.52 g (81.3%) and purity about 99.3–99.5%.

Preparation C PMPA (0.50 g) is optionally recrystallized from about 7.5 mL boiling H$_2$O (15:1 wt. ratio). Upon cooling to room temperature, the PMPA is filtered on a coarse frit fit with Tyvek™. The filter cake is rinsed with ice-cold H$_2$O and acetone then sucked to dryness to afford a fluffy white solid. The filtrate is optionally also concentrated to afford a white solid. PMPA prepared from one or more recrystallizations is optionally used to make PMPA derivatives.

Step 7. Bis(POC)PMPA fumarate: Reaction of PMPA, a base such as a trialkylamine (TEA, diisopropyl ethyl amine) and chloromethyl-2-propyl carbonate in a suitable solvent such as NMP yields bis(POC)PMPA. Moderate agitation of the reactants used with a reaction temperature of about 55–80° for about 1–6 hours typically gives good bis(POC) PMPA yields. The bis(POC)PMPA synthesis reaction gives good results under a variety of conditions within these time and temperature ranges. For example, the reaction gives good results when a lower temperature reaction (about 55–65°) follows an initial high temperature reaction (about 70–80, but no more than 80°) for a short period (about 30–120 minutes). Exemplary reactions are (1) 30 minutes at 80°, followed by reaction at 60–65° for 2 hours, (2) about 4 hours at 60° and (3) 2 hours at 70–72°.

After the bis(POC)PMPA synthesis reaction is completed, one optionally uses filtration to remove solids from the reaction mixture, followed by washing with an alkyl acetate, usually the acetate of a C$_{1-4}$ alkyl moiety, e.g., n-butyl acetate, n-propyl acetate, isopropyl acetate or ethyl acetate. Next, in vacuo distillation removes organic solvents to about 30% of the original reaction volume. Addition of fumaric acid allows formation of solid BPPF, which precipitates, usually as cBPPF. The BPPF or cBPPF may contain small amounts, usually less than 1% (about 0.2–0.4%), of water or organic solvent such as 1-methyl-2-pyrrolidinone, a trialkylamine (e.g., C$_{1-3}$ alkyl such as triethylamine, methyldiethylamine, diisopropyl ethyl amine, or propyldiethylamine), methyl acetate, ethyl acetate, propyl acetate, isopropyl acetate, a C$_{1-6}$ alkanol, pyridine, dimethylformamide, dimethylsulfoxide, acetone, CH$_2$Cl$_2$, tetrahydrofuran, acetonitrile, toluene, a xylene, methyl ethyl ketone, 1,2-dichloroethane or CHCl$_3$. Typically the fumaric acid is dissolved in a C$_{1-6}$ alkanol such as n-hexanol, n-pentanol, n-butanol, isopropanol, n-propanol, ethanol or methanol.

Methods and compositions used to make BPPF or cBPPF use bis(POC)PMPA and fumaric acid, which are contacted as reactants. Generally one will use a solution containing at about 3–430 mg/mL bis(POC)PMPA, usually about 4–100 mg/mL. Generally one will use a bis(POC)PMPA:fumaric acid molar ratio of about 0.6:1–1.4:1, usually about 0.9:1.1 or about 1:1. Generally the solutions used comprise an organic solvent such as an alkyl acetate, 1-methyl-2-pyrrolidinone, a trialkylamine, a C$_{1-6}$ alkanol, pyridine, dimethylformamide, dimethylsulfoxide, acetone, CH$_2$Cl$_2$, tetrahydrofuran, acetonitrile, toluene, a xylene, methyl ethyl ketone, 1,2-dichloroethane or CHCl$_3$.

In an embodiment, synthesis of bis(POC)PMPA and crystallization with fumaric acid to form BPPF, is shown in above as step 7 and is described as follows. In a reactor with an inert atmosphere, e.g., nitrogen, a mixture of 1-methyl-2-pyrrolidinone (4.12 kg), PMPA monohydrate (1.00 kg), and triethylamine (0.996 kg), are agitated for about 15–45 min., typically about 30 min, and then chloromethyl-2-propyl carbonate (2.50 kg) is added and the mixture is heated to about 55–65° C., typically about 60° C. and agitated without splashing the contents for about 3–6 hours, typically about 4 hours, until the reaction is complete, as optionally indicated by HPLC (no more than 15% mono (POC)PMPA present). The mixture is diluted with isopropyl acetate (10.72 kg), cooled to about 15–30° C., typically about 25° C., as rapidly as possible, and while holding the reactor contents at about 15–30° C., typically at about 25° C., the mixture is agitated for about 20–60 minutes, typically about 30 minutes. The solids are removed by filtration and washed with isopropyl acetate (4.44 kg). The combined organic phases at about 15–30° C., typically about 25° C., are extracted twice with water (3.28 kg per wash) using moderate agitation for about 1–10 min. to avoid forming an emulsion followed by allowing the phases to separate. The combined aqueous phases are back-extracted twice with isopropyl acetate (3.56 kg per wash) (about 15–30° C., typically about 25° C.). All organic phases are combined and washed with water (2.20 kg) (about 15–30° C., typically about 25° C.) using moderate agitation for about 1–10 min. to avoid forming an emulsion. The combined organic phases, which are at about 25–43° C., but at no more than 45° C., are concentrated in vacuo (about 26.5–28"Hg) to approximately 30% of the original volume (about 10–12 L/kg PMPA monohydrate). After a polishing filtration using an in-line 1 μm filter, the concentration of the organic phase is resumed at about 20–38° C., but no higher than 40° C. under a vacuum (about 28"Hg) until a pale yellow oil remains. The oil is dissolved in a warmed solution (about 45–55° C., typically about 50° C.) of fumaric acid (0.38 kg) in 2-propanol (6.24 kg) with vigorous agitation until solids dissolve, about 0.5–2.0 hours. The warm solution is then optionally filtered using an in-line 1 μm filter while minimizing cooling of the solution. The filtrate at about 34–50° C., typically at about 40° C., is agitated using the minimum agitation needed to obtain a homogenous solution. The resulting solution is cooled to about 30–33° C., typically about 32° C., over about 30 minutes using minimal agitation, optionally seeded with a small quantity of bis(POC)PMPA fumarate (about 100 mg), and cooled to about 12–18° C., typically about 15° C., over about 1–2 hours, typically over about 1 hour. Seed crystals may not be needed if crystal formation begins before seed crystals are added. Crystals form over a range of about 12–33° C. as the solution is cooled. Agitation is discontinued when crystal formation begins. The mixture is allowed to stand at about 15° C. for at least about 12 hours, typically about 12–30 hours. The resulting slurry is filtered (Tyvek™) and the filter cake is washed with a premixed solution of isopropyl acetate (0.70 kg) in butyl ether (2.44 kg) (1:4 v/v). The filter cake, which is at no more than 40° C., is dried in vacuo for about 1 to 10 days and the dried product is optionally milled (Fitzmill M5A fitted with a 0.050" screen), affording bis(POC)PMPA fumarate as white, fine, powder-like crystals of about 97.0 to 99.5% purity. The BPPF is optionally recrystallized essentially as described here to increase product purity if desired.

Embodiments include compositions that transiently occur when a method step or operation is performed. For example, when a lithium alkoxide is mixed with a 9-(2-hydroxypropyl)adenine solution, the composition at the initiation of mixing will contain negligible amounts of the lithium alkoxide. This composition will be generally be present as a non-homogenous mixture prior to sufficient agitation to mix the solution. Such a composition usually comprises negligible reaction products and comprises mostly reactants. Similarly, as a reaction proceeds, the proportions of reactants, products and by-products will change relative to each other. These transient compositions are intermediates that arise when a process step is performed and they are expressly included as invention embodiments.

All citations found herein are incorporated by reference with specificity.

The following examples further illustrate but do not limit the invention.

EXAMPLES

Example 1

Bis(POC) PMPA fumarate physical properties. The X-ray powder diffraction pattern of cBPPF was determined using a General Electric model XRD-5 X-ray diffractometer and a Siemens Software Systems interface at a scanning speed of two degrees 2-theta (2θ) per minute according to a published procedure (U.S. Pharmacopoeia, vol. 23, 1995, method 941, U.S.P. Pharmacopeial Convention, Inc, Rockville, Md.). The BPPF crystals were scanned between 4 and 35 degrees 2θ by exposure to an X-ray generator operated at 40 KV and at –20 mA using a standard focus copper X-ray tube (Varican CA-8) with a graphite monochromator (ES Industries) and a scintillation detector. The weighted mean values of X-ray wavelengths used for the calculations were CuKα 1.541838 Å. BPPF exhibits characteristic X-ray powder diffraction peaks expressed in degrees 2θ at approximately 4.9, 10.2, 10.5, 18.2, 20.0, 21.9, 24.0, 25.0, 25.5, 27.8, 30.1 and 30.4. An exemplary X-ray powder diffraction pattern is shown below.

BPPF crystals were also analyzed by differential scanning calorimetry and exhibited a thermogram with a characteristic peak at approximately 118.3° C., having an onset at approximately 116.1° C. The thermogram was obtained using a scan rate of 10° C. per minute under a nitrogen atmosphere. The calorimetry scan was obtained using a differential scanning calorimeter (TA Instruments, model DSC 2910 with a model 2200 controller). Approximately 5 mg of BPPF crystals were used to obtain the thermogram. Differential scanning calorimetry has been described (see, e.g., U.S. Pharmacopoeia, vol. 23, 1995, method 891, U.S.P. Pharmacopeial Convention, Inc, Rockville, Md.).

The melting point, the temperature at which a test sample becomes liquid throughout, of BPPF was determined using a Mettler FP81 measuring cell equipped with a FP90 central processor, according to a published procedure (U.S. Pharmacopoeia vol. 22, 1994, method 741, method Ia, U.S.P. Pharmacopeial Convention, Inc, Rockville, Md.). The bottom of a capillary glass tube was filled with finely ground BPPF. The BPPF was compacted to 4–6 mm by tapping the capillary tube on a hard surface. The capillary tube was loaded into the sample slot and the temperature was increased at a rate of 1° C. per minute. The melting point, 114.2 to 114.6° C., was based on the temperature at which sample melting was complete.

BPPF was tested for water content by Karl Fischer titration using a Metrohm 684 KF Coulometer according to a published procedure (U.S. Pharmacopoeia, vol. 23, 1995, method 921, U.S.P. Pharmacopeial Convention, Inc, Rockville, Md.) and manufacturer's Coulometer instructions. The amount of BPPF used in the assay, about 50–100 mg, was measured using a five place analytical balance (Sartorius, Model RC210D, or equivalent). A typical batch contained less than 1.0% w/w water.

BPPF crystals were analyzed by infrared spectrophotometry using a Perkin-Elmer model 1650 FT-IR spectrophotometer according the manufacturer's instructions. KBr (Aldrich, IR grade) was dried overnight at 60° C. under vacuum before use. A translucent pellet containing about 10% by weight (about 5 mg) of BPPF crystals and about 90% by weight (50 mg) of dried KBr was prepared by grinding the two powders together to obtain a fine powder. IR spectroscopy has been described (see, e.g., U.S. Pharmacopoeia, vol. 22, 1994 method 197, U.S.P. Pharmacopeial Convention, Inc, Rockville, Md.; Morrison, R. T. et al, *Organic Chemistry*, 3rd ed., Allyn and Bacon, Inc., Boston, p 405–412, 1973). The spectrophotometer sample chamber was purged for at least 5 minutes with high purity nitrogen gas at about 6 p.s.i. to reduce carbon dioxide absorbance interference to ≦3% in a background scan prior to scanning with the sample. BPPF crystals exhibited an infrared absorption spectrum in potassium bromide with characteristic bands expressed in reciprocal centimeters at approximately 3224 (O—H), 3107–3052 (N—H, C=C—H), 2986–2939 (aliphatic C—H), 1759 (alkyl ester C=O), 1678 (aromatic C=N), 1620 (aromatic C=C), 1269 (phosphonate P=O) and 1102 (C—O—C).

The solubility of BPPF in different solvents was examined. BPPF was found to be generally most soluble in polar solvents, which are typically used in the invention methods and embodiments. BPPF solubility in dimethylformamide was 428 mg/mL and BPPF solubility in isopropyl acetate-:water (1:1 v/v), methanol, ethanol, isopropanol, 0.1N HCl and acetone was about 15–100 mg/mL. BPPF solubility in acetonitrile, isopropyl acetate and deionized water (pH 3.3) was about 3–15 mg/mL. BPPF had a low solubility in $CH_2CL_2$, diethyl ether and hexane.

BPPF crystals were analyzed by ultraviolet spectrophotometry using a Hewlett-Packard model 8425A diode array spectrophotometer according the manufacturer's instructions. The amount of BPPF used in the assay, about 25 mg, was measured using a five place analytical balance (Sartorius, Model RC210D, or equivalent) and HPLC or spectrophotometric grade solutions. The molar absorptivity of 10 μg/mL BPPF at pH 6.0 in 0.01M potassium phosphate buffer was 14930 $M^{-1}$ $cm^{-1}$ and 15010 $M^{-1}$ $cm^{-1}$ at pH 2.0 in 0.01N HCl for 15 μg/mL BPPF. BPPF (10 μg/mL) in methanol had a λmax at about 260 nm.

BPPF crystals were not hygroscopic when kept at 92% relative humidity and at room temperature for up to 37 days. BPPF has a pKa of 3.8 as determined by potentiometric titration.

Example 2

Chiral enrichment of (R)-PMPA. (R,S)-PMPA.$H_2O$ (2.5 g, about 93% R isomer) was suspended in a flask containing water (100 mL) and the pH was adjusted to 7.12 using HCl or NaOH as needed. The solution was warmed to 40° C. and the pH was adjusted to about 5.0. The pH was then adjusted to 3.1, and the solution was seeded with (R)-PMPA. The solution was allowed to cool to room temperature and left for about 2 hours. The solids were collected on a coarse glass frit sintered glass funnel, washed with ice cold water (10 mL) and then washed with acetone (10 mL). The resulting PMPA consisted of 98.3% of the (R) isomer. No chiral enrichment of the (R) isomer was observed when similar protocols were performed using 2.5 g of (R,S)-PMPA (about 93% (R)-isomer) and 25 mL of water. Chiral enrichment of the (R) isomer to 99.6% (R)-isomer was observed when a similar protocol was performed using 0.766 g of (R,S)-PMPA (about 93% (R)-isomer) and 10 mL of water.

Example 3

The solid state chemical stability of cBPPF and bis(POC) PMPA-citrate salt was compared by analyzing each compound after storage under different conditions. The results showed that BPPF powder was unexpectedly more stable to storage at elevated temperature and relative humidity.

| Conditions | time* | BPPF % | mono(POC) PMPA fumarate % | bis(POC) PMPA citrate % | mono(POC) PMPA citrate % |
|---|---|---|---|---|---|
| 40° C., 75%** | 0 | 99.0 | 1.0 | 99.0 | 1.0 |
| | 14 | 98.3 | 1.7 | 96.9 | 3.1 |
| | 30 | 98.1 | 1.9 | 92.9 | 7.1 |
| | 60 | 97.1 | 2.9 | 77.6 | 22.4 |
| 60° C., 75% | 0 | 99.0 | 1.0 | 99.0 | 1.0 |
| | 3 | 96.9 | 3.1 | 24.0 | 58.9*** |
| | 7 | — | — | 6.7 | 76.2*** |
| | 11 | 90.4 | 9.6 | — | — |
| | 15 | 81.3 | 18.7 | — | — |

*days,
**relative humidity,
***other products were generated in addition to mono(POC)PMPA citrate Example 4

Formulation of bis(POC)PMPA fumarate. Crystalline BPPF was formulated with several excipients as follows.

| Component | % w/w | per unit content (mg/tablet) |
|---|---|---|
| BPPF | 34.0 | 75 |
| Lactose Monohydrate, NF | | |
| intragranular portion | 54.0 | 119.2 |
| extragranular portion | 2.0 | 4.4 |
| Pregelatinized starch, NF | 5.0 | 11.0 |
| Croscarmellose Sodium, NF | | |
| intragranular portion | 2.0 | 4.4 |
| extragranular portion | 2.0 | 4.4 |
| Magnesium Stearate, NF | 1.0 | 2.2 |

In the formulation, pregelatinized starch NF was used as a binder and disintegrant suitable for tablet compression. Croscarmellose sodium NF, which is internally cross-linked sodium carboxymethylcellulose, was used to facilitate tablet disintegration and dissolution. Lactose monohydrate NF was used as a diluent to aid manufacturing and to facilitate tablet dissolution. Magnesium stearate NF was used as a lubricant to facilitate tablet ejection from the tablet compression process.

Tablets containing BPPF are made by blending pregelatinized starch, croscarmellose sodium and lactose monohydrate in a blender. Water is added until a suitable wet granulation is formed. The wet granulation is milled, dried in a fluid bed dryer to a moisture content of not more than 3% loss on drying and the dried granules are passed through a mill. The milled granules are combined with extragranular excipients, croscarmellose sodium and lactose monohydrate, and blended in a mixer to obtain a powder blend. The powder blend is then blended with magnesium stearate and then compressed into tablets. The tablets are filled into high density polyethylene or glass bottles along with polyester fiber packing material and optionally with a silica gel desiccant.

We claim:

1. A composition of formula (1)

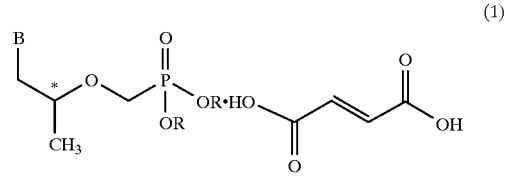

(1)

wherein B is adenin-9-yl and R independently is —H or —CH$_2$—O—C(O)—O—CH(CH$_3$)$_2$, but at least one R is —CH$_2$—O—C(O)—O—CH(CH$_3$)$_2$.

2. The composition of claim 1 wherein both R are —CH$_2$—O—C(O)—O—CH(CH$_3$)$_2$.

3. The composition of claim 1 wherein the composition is a crystalline solid.

4. The composition of claim 1 wherein the compound is enriched or resolved at the carbon atom chiral center (*).

5. The composition of claim 1 having an X-ray powder diffraction spectrum peak using Cu-Kα radiation, expressed in degrees 2θ at about 25.0.

6. A composition comprising the composition of claim 1 and an acceptable excipient.

7. A composition comprising a lithium alkoxide and a 9-(2-hydroxypropyl)adenine solution.

8. A composition comprising an (R,S)-PMPA solution at a pH of about 2.7–3.5 wherein the solution has less than about 0.1 g/mL (R,S)-PMPA and wherein about 90–94% of the PMPA is in the (R) configuration.

9. A method comprising orally administering to a patient infected with virus or at risk to viral infection a therapeutically effective amount of a composition of claim 1.

10. A method comprising contacting bis(POC)PMPA with fumaric acid.

11. The method of claim 10 wherein the fumaric acid is dissolved in 2-propanol.

12. A method comprising mixing a lithium alkoxide with a 9-(2-hydroxypropyl)adenine solution.

13. The method of claim 12 wherein the lithium alkoxide is an alkoxide selected from the group consisting of methoxide, ethoxide, n-propoxide, i-propoxide, n-butoxide, i-butoxide, t-butoxide, neopentoxide, n-pentoxide, i-pentoxide or n-hexoxide, n-heptoxide, 2-heptoxide, n-octoxide, 2-octoxide, typically t-butoxide or i-propoxide.

14. The method of claim 13 wherein the lithium alkoxide is lithium t-butoxide or lithium i-propoxide.

15. A method comprising adjusting the pH of a solution comprising less than about 0.08 g/mL (R,S)-PMPA wherein about 90–94% of the PMPA is in the (R) configuration to a pH of about 2.7–3.5.

16. A composition comprising a tablet containing 9-[2-(R)-[[bis[[(isopropoxycarbonyl)oxy]methoxy]phosphinoyl]methoxy]propyl]-adenine.fumaric acid (1:1), pregelatinized starch, croscarmellose sodium, lactose monohydrate and magnesium stearate.

17. The composition of claim 16 wherein the 9-[2-(R)-[[bis[[(isopropoxycarbonyl)oxy]methoxy]phosphinoyl]methoxy]propyl]-adenine.fumaric acid (1:1) is crystalline.

18. The composition of claim 16 wherein the tablet contains 75 mg 9-[2-(R)-[[bis[[(isopropoxycarbonyl)oxy]methoxy]phosphinoyl]methoxy]propyl]-adenine.fumaric acid (1:1), 11 mg pregelatinized starch, 8.8 mg croscarmellose sodium, 123.6 mg lactose monohydrate and 2.2 mg magnesium stearate.

19. A product produced by the process of preparing wet granules from a mixture comprising a liquid, 9-[2-(R)-[[bis[[(isopropoxycarbonyl)oxy]methoxy]phosphinoyl]methoxy]propyl]-adenine.fumaric acid (1:1) and a pharmaceutically acceptable excipient.

20. The product of claim 19 wherein the liquid is water and the process optionally further comprises drying the wet granules.

* * * * *

UNITED STATES PATENT AND TRADEMARK OFFICE
CERTIFICATE OF CORRECTION

PATENT NO.        : 5,935,946 C1                                    Page 1 of 1
APPLICATION NO.   : 90/008556
DATED             : October 14, 2008
INVENTOR(S)       : Munger, Jr. et al.

It is certified that error appears in the above-identified patent and that said Letters Patent is hereby corrected as shown below:

At column 1, line 30 of the Reexamination Certificate, please replace "1) $(CH_2O)N/Et_3N$/toluene" with --1) $(CH_2O)_n/Et_3N$/toluene--.

At column 1, line 43 of the Reexamination Certificate, please replace "1BuOLi" with --$^tBuOLi$--.

At column 4, line 2 or the Reexamination Certificate, please replace "has" with --had--.

Signed and Sealed this

Seventeenth Day of March, 2009

JOHN DOLL
*Acting Director of the United States Patent and Trademark Office*

(12) EX PARTE REEXAMINATION CERTIFICATE (6474th)
United States Patent
Munger, Jr. et al.

(10) Number: US 5,935,946 C1
(45) Certificate Issued: Oct. 14, 2008

(54) NUCLEOTIDE ANALOG COMPOSITION AND SYNTHESIS METHOD

(75) Inventors: John D. Munger, Jr., Alviso, CA (US); John C. Rohloff, Mountain View, CA (US); Lisa M. Schultze, San Carlos, CA (US)

(73) Assignee: Gilead Sciences, Inc., Foster City, CA (US)

Reexamination Request:
No. 90/008,556, Apr. 30, 2007

Reexamination Certificate for:
Patent No.: 5,935,946
Issued: Aug. 10, 1999
Appl. No.: 08/900,752
Filed: Jul. 25, 1997

(51) Int. Cl.
*C07F 9/00* (2006.01)
*C07F 9/6561* (2006.01)
*C07D 473/00* (2006.01)
*C07D 473/34* (2006.01)
*A61K 31/675* (2006.01)

(52) U.S. Cl. .......................... 514/81; 544/244
(58) Field of Classification Search .................. None
See application file for complete search history.

(56) References Cited

U.S. PATENT DOCUMENTS 5,922,695 A 7/1999 Arimilli et al.

FOREIGN PATENT DOCUMENTS

EP 0 632 048 A1 1/1995

OTHER PUBLICATIONS

Handbook of Pharmaceutical Excipients, pp. 153–162, 296–297, 1986.*
Osol et al., Editor, Remington's Pharmaceutical Sciences, Sixteenth Edition, pp. 1554–1557, 1980.*
Martindale The Extra Pharmacopoeia, Twenty–eighth Edition, pp. 950–951, compound No. 5411–b, 1982.*
Bischofberger et al., Bis(POC)PMPA, an Orally Bioavailable Prodrug of the Antiretroviral Agent PMPA, Conference on Retroviruses and Opportunistic Infections, 4th:104 (abstract No. 214), Jan. 22–26, 1997.
Gould, Salt Selection for Basic Drugs, International Journal of Pharmaceutics, 33:201–271, 1986.

* cited by examiner

*Primary Examiner*—Dwayne C Jones

(57) ABSTRACT

The invention provides a composition comprising bis(POC) PMPA and fumaric acid (1:1). The composition is useful as an intermediate for the preparation of antiviral compounds, or is useful for administration to patients for antiviral therapy or prophylaxis. The composition is particularly useful when administered orally. The invention also provides methods to make PMPA and intermediates in PMPA synthesis. Embodiments include lithium t-butoxide, 9-(2-hydroxypropyl) adenine and diethyl p-toluenesulfonylmethoxyphosphonate in an organic solvent such as DMF. The reaction results in diethyl PMPA preparations containing an improved by-product profile compared to diethyl PMPA made by prior methods.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 8, line 42 to columns 9/10, line 39:

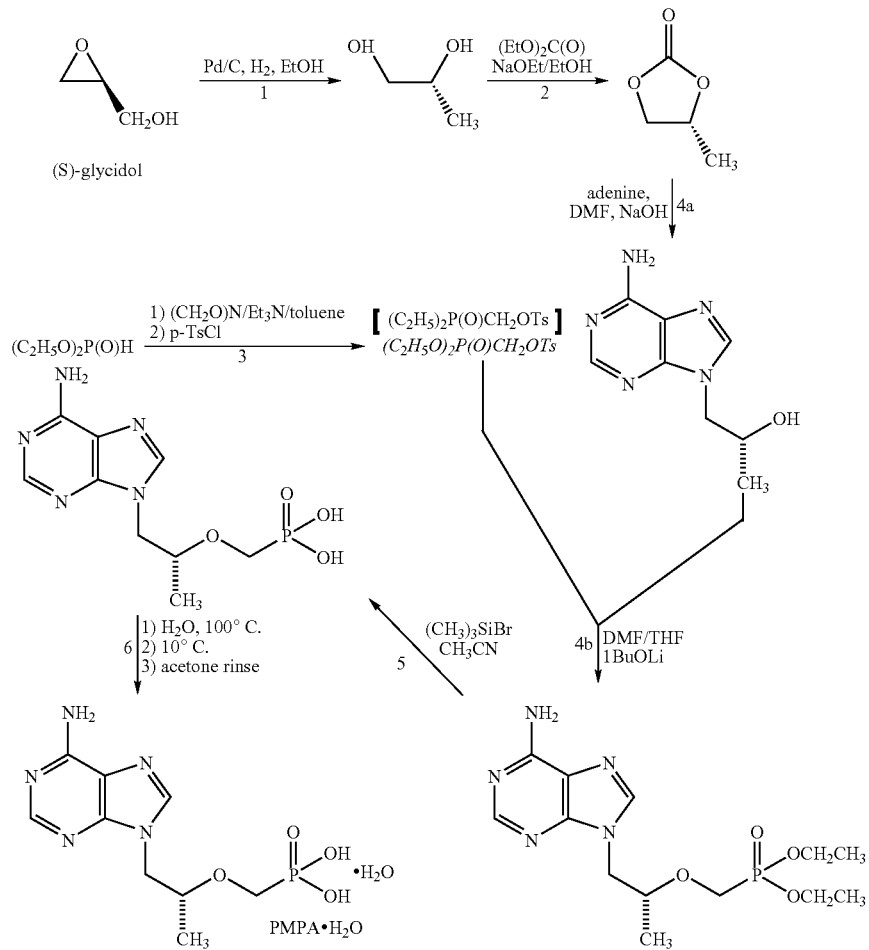

Column 16, line 63 to column 17, line 9:

Embodiments include compositions that transiently occur when a method step or operation is performed. For example, when a lithium alkoxide is mixed with a 9-(2-hydroxypropyl)adenine solution, the composition at the initiation of mixing will contain negligible amounts of the lithium alkoxide. This composition will [be] generally be present as a non-homogenous mixture prior to sufficient agitation to mix the solution. Such a composition usually comprises negligible reaction products and comprises mostly reactants. Similarly, as a reaction proceeds, the proportions of reactants, products and by-products will change relative to each other. These transient compositions are intermediates that arise when a process step is performed and they are expressly included as invention embodiments.

Column 18, line 4 to column 18, line 26:

BPPF crystals were analyzed by infrared spectrophotometry using a Perkin-Elmer model 1650 FT-IR spectrophotometer according *to* the manufacturer's instructions. KBr (Aldrich, IR grade) was dried overnight at 60° C. under vacuum before use. A translucent pellet containing about 10% by weight (about 5 mg) of BPPF crystals and about 90% by weight (50 mg) of dried KBr was prepared by grinding the two powders together to obtain a fine powder. IR spectroscopy has been described (see, e.g., U.S. Pharmacopoeia, vol. 22, 1994 method 197, U.S.P. Pharmacopeial Convention, Inc, Rockville, Md.; Morrison, R. T. et al, Organic Chemistry, 3rd ed., Allyn and Bacon, Inc., Boston, p 405–412, 1973). The spectrophotometer sample chamber was purged for at least 5 minutes with high purity nitrogen gas at about 6 p.s.i. to reduce carbon dioxide absorbance interference to $\leq 3\%$ in a background scan prior to scanning with the sample. BPPF crystals exhibited an infrared absorption spectrum in potassium bromide with characteristic bands expressed in reciprocal centimeters at approximately 3224 (O—H), 3107-3052 (N—H, C=C—H), 2986-2939 (aliphatic C—H), 1759 (alkyl ester C=O), 1678

(aromatic C=N), 1620 (aromatic C=C), 1269 (phosphonate P=O) and 1102 (C—O—C).

Column 18, lines 37–47:

BPPF crystals were analyzed by ultraviolet spectrophotometry using a Hewlett-Packard model 8425A diode array spectrophotometer according *to* the manufacturer's instructions. The amount of BPPF used in the assay, about 25 mg, was measured using a five place analytical balance (Sartorius, Model RC210D, or equivalent) and HPLC or spectrophotometric grade solutions. The molar absorptivity of 10 μg/mL BPPF at pH 6.0 in 0.01M potassium phosphate buffer was 14930 $M^{-1}$ $cm^{-1}$ and 15010 $M^{-1}$ $cm^{-1}$ at pH 2.0 in 0.01N HCl for 15 μg/mL BPPF. BPPF (10 μg/mL) in methanol has a λmax at about 260 nm.

AS A RESULT OF REEXAMINATION, IT HAS BEEN DETERMINED THAT:

The patentability of claims 1–7, 9–14 and 16–18 is confirmed.

Claims 8, 15, 19 and 20 are cancelled.

* * * * *